(12) United States Patent
DeMarco

(10) Patent No.: US 7,351,332 B2
(45) Date of Patent: Apr. 1, 2008

(54) CHROMATOGRAPHY CARTRIDGE AND METHOD FOR MANUFACTURING A CHROMATOGRAPHY CARTRIDGE

(75) Inventor: Nicholas DeMarco, Twin Lakes, WI (US)

(73) Assignee: Varian, Inc., Palo Alto, CA (US)

( * ) Notice: Subject to any disclaimer, the term of this patent is extended or adjusted under 35 U.S.C. 154(b) by 0 days.

(21) Appl. No.: 10/775,451

(22) Filed: Feb. 10, 2004

(65) Prior Publication Data

US 2005/0082213 A1   Apr. 21, 2005

Related U.S. Application Data

(60) Provisional application No. 60/512,129, filed on Oct. 17, 2003.

(51) Int. Cl.
*B01D 15/08* (2006.01)
(52) U.S. Cl. ............ 210/198.2; 210/232; 210/282; 210/635; 210/656; 156/73.5; 264/248
(58) Field of Classification Search ............ 210/198.2, 210/635, 656, 232, 282; 96/101, 103, 106; 95/82; 156/73.5; 264/248
See application file for complete search history.

(56) References Cited

U.S. PATENT DOCUMENTS

| | | | | |
|---|---|---|---|---|
| 4,250,141 A | * | 2/1981 | Lehmann et al. ............ | 422/44 |
| 4,626,350 A | * | 12/1986 | Reid ............................ | 210/282 |
| 5,059,654 A | * | 10/1991 | Hou et al. .................. | 525/54.1 |
| 5,256,284 A | * | 10/1993 | Lee ............................. | 210/232 |
| 5,360,544 A | * | 11/1994 | Nakaso et al. ............... | 210/483 |
| 5,591,332 A | * | 1/1997 | Reid et al. ................... | 210/235 |
| 5,601,708 A | | 2/1997 | Leavesley | |
| 5,693,223 A | * | 12/1997 | Yamada et al. .......... | 210/198.2 |
| 6,001,253 A | | 12/1999 | Conroy et al. | |
| 6,068,766 A | | 5/2000 | Van Davelaar | |
| 6,074,556 A | | 6/2000 | Van Davelaar | |
| 6,090,278 A | | 7/2000 | Lally et al. | |
| 6,117,329 A | | 9/2000 | Hargro | |
| 6,132,605 A | | 10/2000 | Leavesley et al. | |
| 6,139,733 A | | 10/2000 | Hargro et al. | |

(Continued)

OTHER PUBLICATIONS

Snyder (Introduction to Modern Liquid Chromatography, John Wiley, New York, 1979, pp. 21-22 and 410-414).*

(Continued)

*Primary Examiner*—Ernest G. Therkorn
(74) *Attorney, Agent, or Firm*—Michael Best & Friedrich LLP

(57) ABSTRACT

A chromatography cartridge and method of manufacturing same. A chromatography cartridge of the present invention can include a tubular housing having an open end and an inner surface, and a plug. The plug can be positioned within the open end of the tubular housing and can have an outer circumferential surface, a substantial portion of the outer circumferential surface being fused to the inner surface of the tubular housing. A method for manufacturing a chromatography cartridge can include coupling at least a portion of the outer surface of the plug to at least a portion of the inner surface of the tubular housing in response to rotating at least one of the plug and the tubular housing about the longitudinal axis with respect to the other of the plug and the tubular housing.

26 Claims, 3 Drawing Sheets

U.S. PATENT DOCUMENTS

| | | |
|---|---|---|
| 6,171,486 B1 | 1/2001 | Green et al. |
| 6,221,252 B1 | 4/2001 | Hargro et al. |
| 6,280,619 B1 * | 8/2001 | Lacy et al. .................. 210/232 |
| 6,294,087 B1 | 9/2001 | Hargro et al. |
| 6,398,953 B1 | 6/2002 | Hargro |
| 6,436,284 B1 | 8/2002 | Leavesley et al. |
| 6,454,891 B1 * | 9/2002 | Goss ......................... 156/73.5 |
| 6,565,745 B2 | 5/2003 | Hodgin et al. |
| 6,632,355 B2 * | 10/2003 | Fritze ......................... 210/232 |
| 6,949,194 B2 | 9/2005 | Hodgin et al. |
| 6,953,526 B1 * | 10/2005 | Fritze ......................... 210/234 |
| 7,008,541 B2 * | 3/2006 | Hodgin et al. ............... 210/656 |
| 2003/0010698 A1 * | 1/2003 | Fritze ......................... 210/235 |
| 2003/0102264 A1 * | 6/2003 | Pope et al. .................. 210/646 |
| 2004/0084375 A1 | 5/2004 | Hodgin et al. |
| 2005/0242018 A1 | 11/2005 | Hodgin et al. |

OTHER PUBLICATIONS

ISCO product brochure #2291: "CombiFlash™ Organic Purification Systems from Isco;" Oct. 1999; 4 pages; Statement of Relevance attached.

* cited by examiner

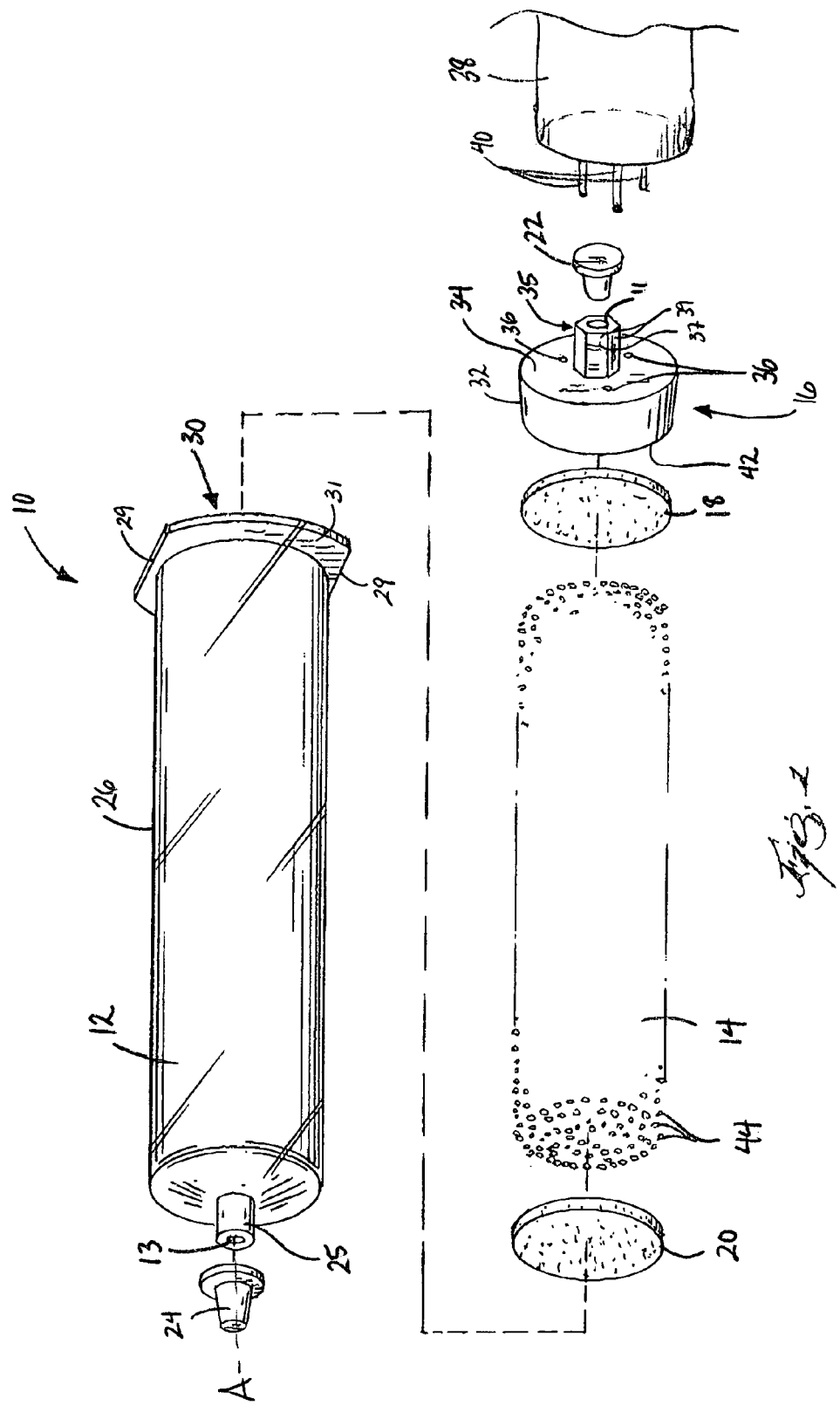

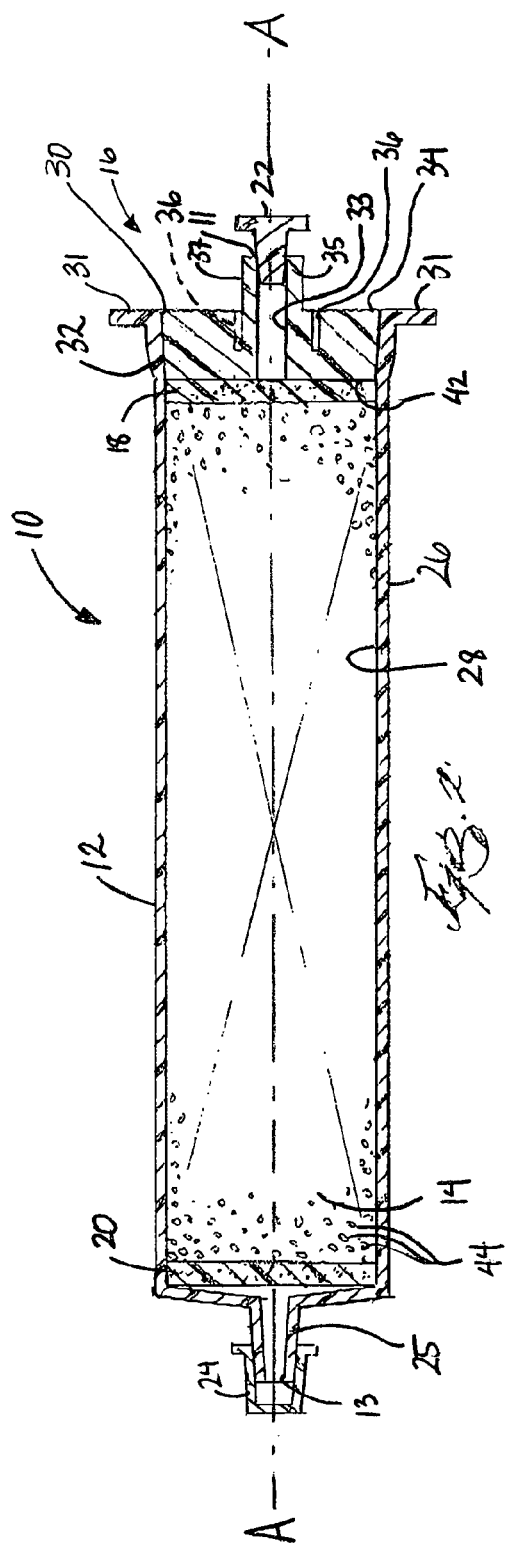
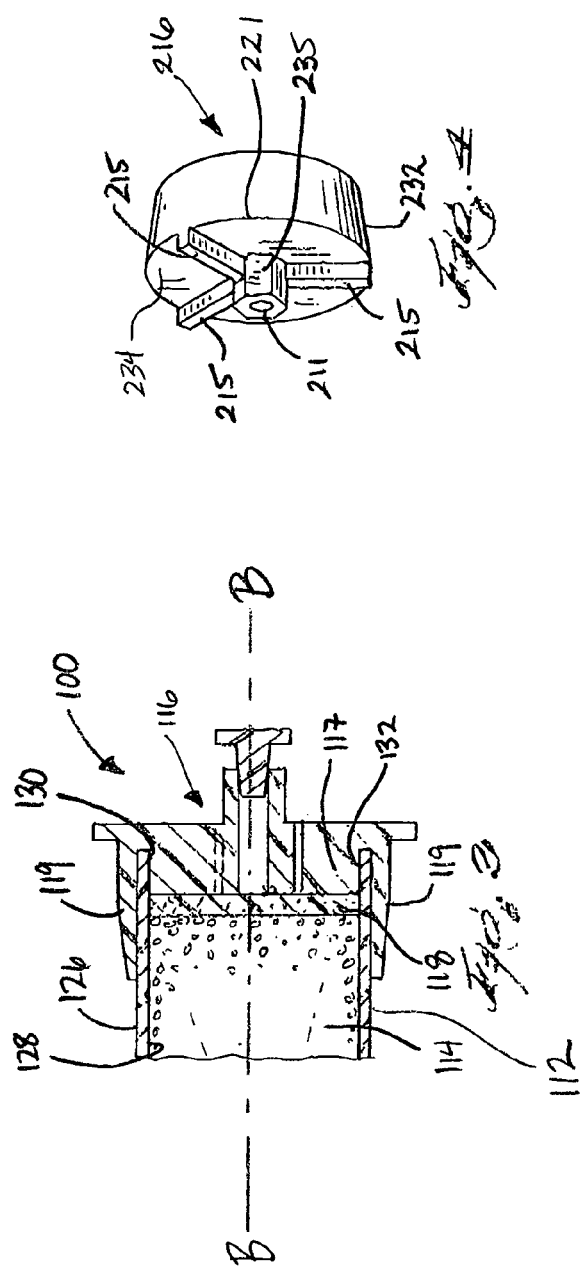

CHROMATOGRAPHY CARTRIDGE AND METHOD FOR MANUFACTURING A CHROMATOGRAPHY CARTRIDGE

RELATED APPLICATIONS

This application claims the benefit of U.S. Provisional Patent Application Ser. No. 60/512,129, filed Oct. 17, 2003.

BACKGROUND OF THE INVENTION

Chromatography columns or cartridges typically contain a densely-packed chromatography media (sometimes referred to as the "stationary phase"). When liquid (sometimes referred to as the "liquid phase") is passed through the chromatography cartridge, at least a portion of the liquid phase adsorbs to the stationary phase within the cartridge. In this way, those components of the liquid phase that adsorb to the stationary phase are separated out from those that do not. Based on the different adsorption rates of various components of the liquid phase, the various components of the liquid phase can be isolated and identified.

When the cartridge is used, "channeling" can result if the media is not tightly packed. If the media is not tightly packed, the liquid phase in the chromatography system may find an "easy" path through the media. That is, the liquid phase may not evenly progress through the stationary phase, but instead flow through discrete "channels" in the media. If an easy flow path is available to the liquid because the media is not tightly packed, the liquid may not interact as desired with the rest of the media. The liquid phase will only interact with the media along the "channels" through which it flows. Therefore, much of the media will not be used, which may affect the performance of the chromatography cartridge and the accuracy of the chromatography results.

SUMMARY OF THE INVENTION

The method used to manufacture a chromatography cartridge can reduce channeling. For example, channeling can be controlled by the method used to couple an endcap to a housing portion of the cartridge. The method of coupling the endcap can affect, among other things, whether a hermetic (leak-proof) seal is established in the cartridge, whether the chromatography media is tightly packed within the cartridge, whether the chromatography media is maximally used in separation of various components of the liquid phase, and whether the chromatography system will produce repeatable, accurate results.

In one embodiment, the present invention comprises a chromatography cartridge. The chromatography cartridge includes a tubular housing having an open end and an inner surface, and a plug. The plug is positioned within the open end of the tubular housing and has an outer circumferential surface. A substantial portion of the outer circumferential surface is fused to the inner surface of the tubular housing.

In another embodiment, the present invention includes a method of manufacturing a chromatography cartridge, the chromatography cartridge comprising a housing having an open end and a longitudinal axis, and a plug dimensioned to be received in the open end of the housing. The method includes coupling at least a portion of the outer surface of the plug to at least a portion of the inner surface of the tubular housing in response to rotating at least one of the plug and the tubular housing about the longitudinal axis with respect to the other of the plug and the tubular housing.

Other features and aspects of the invention will become apparent to those skilled in the art upon review of the following detailed description, claims and drawings.

BRIEF DESCRIPTION OF THE DRAWINGS

FIG. 1 illustrates an exploded perspective view of a chromatography cartridge having a housing and a plug, according to one embodiment of the present invention.

FIG. 2 illustrates an assembled cross-sectional view of the chromatography cartridge of FIG. 1.

FIG. 3 illustrates another embodiment of a plug of a chromatography cartridge of the present invention.

FIG. 4 illustrates another embodiment of a plug of a chromatography cartridge of the present invention.

Figure 5:
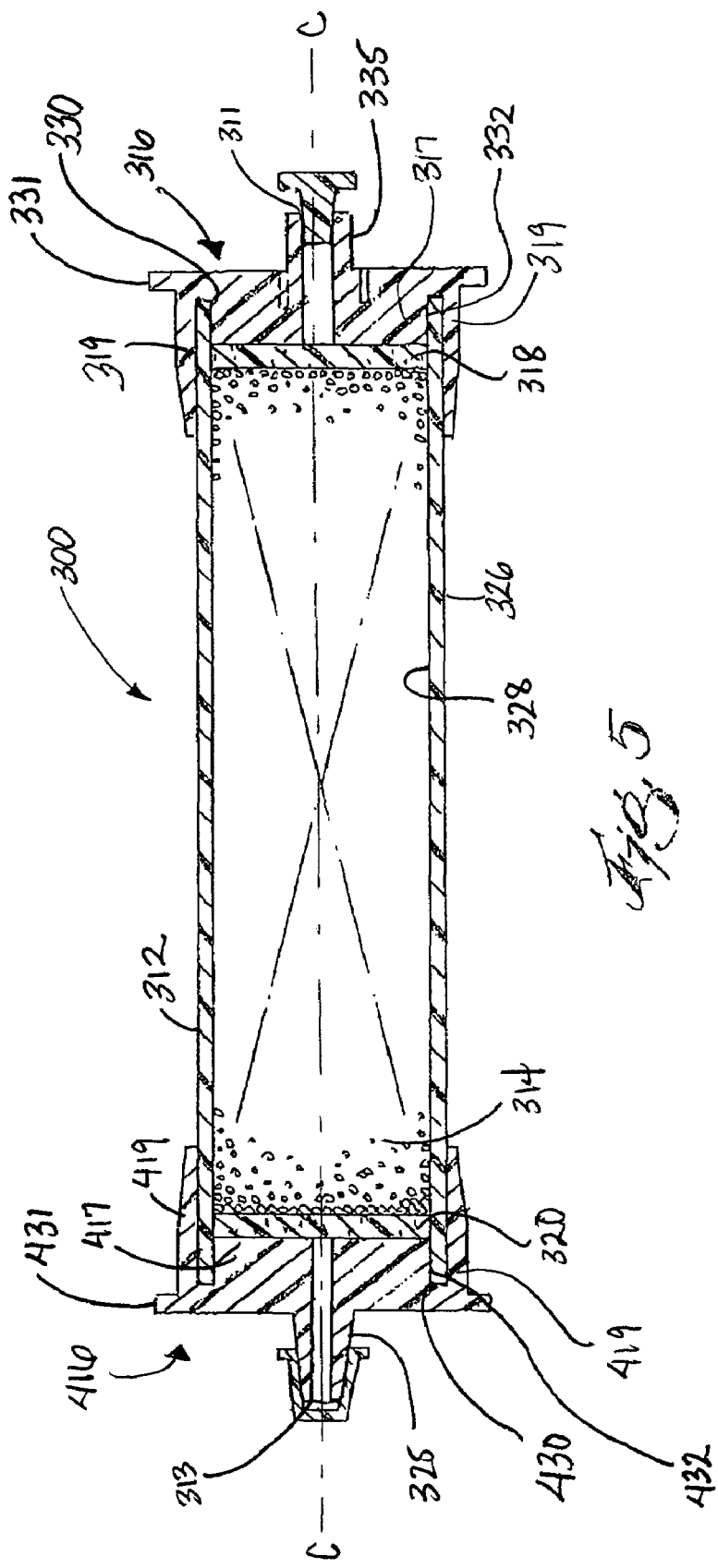
FIG. 5 illustrates another embodiment of a chromatography cartridge of the present invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings.

DETAILED DESCRIPTION

FIGS. 1 and 2 illustrate a chromatography cartridge 10 (also referred to herein as a chromatography "column") according to one embodiment of the present invention. The cartridge 10 contains at least one chromatography medium 14 (also referred to herein as a "stationary phase"), and an inlet 11 and an outlet 13 for fluid flow through the cartridge 10 and thereby the medium 14. The medium 14 is bounded on a first end by a first frit 18 or other porous member positioned towards the inlet 11, and on the second end by a second frit 20 positioned towards the outlet 13. The medium 14 is contained within a housing 12 that is capped on one end by a plug 16 (also referred to herein as and "endcap"). The plug 16 defines the inlet 11 to the cartridge 10. A first cap 22 is dimensioned to be received within the inlet 11 during transportation and storage, and a second cap 24 is dimensioned to cover the outlet 13 during transportation and storage.

The chromatography cartridge 10 can be used with a variety of chromatography systems including, without limitation, a flash chromatography system, and a variety of other liquid chromatography systems. The cartridge 10 can be formed of a variety of materials including without limitation, at least one of a metal, a polymer, a ceramic, a composite, and a combination thereof. As a result, in some embodiments of the present invention, the cartridge 10 can be a long-lasting cartridge that can be used for many chromatography processes. In other embodiments, the cartridge 10 can be formed of disposable materials such that a new chromatography cartridge 10 can be used for each new chromatography run.

In some embodiments, such as the embodiment illustrated in FIG. 1, the housing 12 can have an elongated, tubular shape and a generally uniform and annular cross-section. The housing 12 includes an outer surface 26, an inner surface 28, an open end 30, an annular flange 31 adjacent the open end 30. A longitudinal axis A runs the length of the cartridge 10. The outer surface 26, the inner surface 28 and the open end 30 all have a generally circular shape, as defined by the uniform and annular cross-sectional shape of the housing 12. It should be noted that the cross-sectional shape of the housing 12 can be a variety of other shapes or combinations of shapes without departing from the spirit and scope of the present invention including, without limitation, rectangular, square, triangular, hexagonal, and the like.

With continued reference to FIGS. 1 and 2, the annular flange 31 includes two flat sides 29. However, the annular flange 31 can instead continue around the generally circular open end 30 to form a completely annular flange 31 (i.e., without the flat sides 29). The annular flange 31 can be used to couple the housing 12 to a mechanical drive device during manufacturing of the cartridge 10, as will be described below, to couple the housing 12 to a variety of packing and storage materials for transportation and storage, and/or to couple the housing 12 to other equipment in a chromatography system during use.

As illustrated in FIGS. 1 and 2, the outlet 13 of the cartridge 10 can be defined in the housing 12. A bottom portion of the housing 12 tapers to form an exit tube 25 that defines the outlet 13. As fluid containing at least one sample of interest is injected into a chromatography system, the fluid is moved through the system to the inlet 11 of the cartridge 10, through a central bore 33 of the plug 16 (further described below), through the first frit 18, through the chromatography medium 14 where a variety of components of the fluid may interact with the chromatography medium 14, through the second frit 20, and out the outlet 13 defined in the exit tube 25.

The housing 12 and the plug 16 can be formed of a variety of materials including glass, stainless steel, ceramic, polyethylene, polypropylene, polyethylene terephthalate (PET), polyamide, polyvinyl chloride, polytetrafluoroethylene (e.g., TEFLON®-brand polytetrafluoroethylene (PTFE), DuPont Corporation), a polymer of tetrafluoroethylene and hexafluoropropylene (FEP; e.g., DYNEON™-brand FEP fluorothermoplastic, 3M Corporation), a fiberglass and PTFE composite (e.g., TEFLEX(®-brand fiberglass sheets coated with TEFLON®-brand PTFE, DuPont Corporation), other chemically-inert materials, and the like. The housing 12 and the plug 16 can be formed of the same or different materials.

The plug 16 is dimensioned to be received within the open end 30 of the housing 12. The plug 16 has a generally cylindrical shape and includes an outer circumferential surface 32. The plug 16 further includes a tube 35 extending outwardly from an upper surface 34 of the plug 16, and the tube 35 defines the inlet 11. The plug 16 has an axially-extending central bore 33 such that the plug 16 has a generally annular cross-section, and the inlet 11 provides an opening to the central bore 33.

As illustrated in FIGS. 1 and 2, the tube 35 has a hexagonally-shaped outer surface 37 formed by six sides 39. The hexagonally-shaped outer surface 37 of the tube 35 can provide coupling surfaces for coupling the plug 16 to a mechanical drive device 38 during manufacturing of the cartridge 10, for coupling the plug 16 to packing or storage materials during transportation and storage of the cartridge 10, and/or for coupling the plug 16 to other equipment within a chromatography system during use. In other embodiments, the outer surface 37 can be cylindrical or can include a variety of numbers of sides 39 ranging from three sides 39 to as many as structurally possible. The shape of the outer surface 37 is at least partially dependent upon the chromatography system with which the cartridge 10 is used.

The tube 35 can be integrally formed with the remainder of the plug 16, as shown in FIG. 2, or the tube 35 can be coupled to the upper surface 34 by a variety of fasteners and/or adhesives known to those of ordinary skill in the art.

In some embodiments, the upper surface 34 of the plug 16 can include one or more axially-extending blind bores 36 defined therein and positioned to cooperate with a fixture of a mechanical drive device 38, as described in greater detail below. For example, as illustrated in FIGS. 1-3, the upper surface 34 of the plug 16 includes three axially-extending blind bores 36 positioned around the tube 35. Specifically, the blind bores 36 illustrated in FIG. 1 are arranged such that a blind bore 36 is positioned adjacent every other side 39 of the hexagonally-shaped outer surface 37.

The mechanical drive device 38, as illustrated in FIG. 1, can include three pins 40, each pin 40 dimensioned to be received within an axially-extending blind bore 36, such that upon rotation of the mechanical drive device 38, the cooperation of the pins 40 and the blind bores 36 causes rotation of the plug 16.

In other embodiments, such as the embodiment illustrated in FIG. 4, a plug 216 has an upper surface 234 that includes one or more radially-extending ribs 215 that cooperate with a fixture of a mechanical drive device. The radially-extending ribs 215 can extend outwardly from the upper surface 234 (as shown), or can be formed inwardly (as grooves, not shown) into the upper surface 234. By way of example only, the upper surface 234 of the plug 216 illustrated in FIG. 4 includes three radially-extending ribs 215 that extend outwardly from the upper surface 234. The three radially-extending ribs 215 shown in FIG. 4 are positioned approximately 120° apart from one another about the circular upper surface 234. The three radially-extending ribs 215 each extend radially across the upper surface 234 from a tube 235 that defines an inlet 211 to an edge 221 of the plug 16. In other embodiments, the radially-extending ribs 215 do not necessarily extend all the way to the edge 221, but rather extend radially across a portion of the upper surface 234. In still other embodiments, the radially-extending ribs 215 each have different lengths and extend varying radial distances across the upper surface 234.

A variety of mechanical drive devices can cooperate with the radially-extending ribs 215. For example, the pins 40 of the mechanical drive device 38 shown in FIG. 1 can be moved toward the upper surface 234 of the plug 216 until each pin 40 is either contacting the upper surface 234 or positioned a distance from the upper surface 234 less than the height of each radially-extending rib 215. (Alternatively, if the radially-extending ribs 215 are formed inwardly in the upper surface 234 (i.e., grooves), the pin 40 of the mechanical drive device 38 can be moved until each pin 40 has passed the upper surface 234 or is touching the base of each inwardly-formed rib 215.) Once each pin 40 is positioned near or in contact with the upper surface 234, the mechanical drive device 38 can be rotated. Upon rotation of the mechanical drive device 38, each pin 40 catches on each radially-extending rib 215, and causes the plug 216 to rotate.

As best illustrated in FIG. 2, the chromatography medium 14 is densely packed in the axial space between the first frit 18 and the second frit 20. The cartridge 10 can be manufactured by placing the second frit 20 adjacent the outlet 13 in a bottom portion of the housing 12, filling the housing 12 above the second frit 20 with at least one chromatography medium 14, placing the first frit 18 axially above the chromatography medium 14, and inserting the plug 16 into the open end 30 of the housing 12 to maintain the chromatography medium 14 axially between the first frit 18 and the second frit 20.

The plug 16 is inserted into the open end 30 of the housing 12 until at least a portion of a bottom surface 42 of the plug 16 contacts the first frit 18. By contacting the first frit 18 with at least a portion of the bottom surface 42 of the plug 16, the first frit 18 is maintained in a position that allows the chromatography medium 14 to remain densely packed between the first frit 18 and the second frit 20. Maintaining the first frit 18 at this position can enhance the performance of the chromatography cartridge 20 and can substantially prevent a liquid phase from channeling through the chromatography medium 14 in the cartridge 10.

Referring to FIGS. 1 and 2, the chromatography medium 14 is formed of particles 44. The particles 44 may vary in diameter. For example, particularly in flash chromatography, the diameter of the particles 44 may be specified as 50 μm, but actual particle diameters can range from approximately 32 μm to approximately 63 μm. The volume-to-mass ratio of the particles 44 in a cartridge 10 is referred to herein as the bulk density of the chromatography medium 14. The cartridge 10 can be filled with at least one chromatography medium 14 by volume rather than weight. Some cartridges 10 may have more, but smaller, particles 44 and some may have fewer, but larger, particles 44. Mainly because of this difference, the volume of the chromatography medium 14 filling the housing 12 can vary.

At least a portion of the outer circumferential surface 32 of the plug 16 is fused with the inner surface 28 of the housing 12. Particularly, at least a portion of the inner surface 28, adjacent the open end 30 of the housing 12, is fused to the outer circumferential surface 32 of the plug 16. Fusing at least a portion of the outer circumferential surface 32 of the plug 16 with the inner surface 28 of the housing 12 can maintain the first frit 18 in a desired axial position, can ensure that the at least one chromatography medium 14 remains densely packed throughout a chromatography process, and/or can provide a hermetic seal between the outer circumferential surface 32 of the plug 16 and the inner surface 28 of the housing 12, In the embodiment illustrated in FIGS. 1 and 2, the outer circumferential surface 32 of the plug 16 has been spin-welded to the inner surface 28 of the housing 12. To spin-weld the outer circumferential surface 32 of the plug 16 to the inner surface 28 of the housing 12, at least one of the plug 16 and the housing 12 is coupled to a mechanical drive device, such as the mechanical drive device 38 shown in FIG. 1. For example, the plug 16 can be coupled to the mechanical drive device 38 as explained above, and/or the housing 12 can be coupled to a mechanical drive device by clamping a fixture about the outer surface 26 of the housing 12 and in abutting relation with the annular flange 31.

When the plug 16 and/or the housing 12 are coupled to a mechanical drive device, the mechanical drive device rotates the plug 16 and/or the housing 12 relative to the other of the plug 16 and the housing 12 about the longitudinal axis A. The plug 16 and/or the housing 12 are then axially moved relative to the other to engage the outer circumferential surface 32 of the plug 16 with the inner surface 28 of the housing 12 as the plug 16 and/or the housing 12 continue to be rotated. As the outer circumferential surface 32 of the plug 16 engages the inner surface 28 of the housing 12 while at least one of the plug 16 and the housing 12 are being rotated and moved relative to the other, the outer circumferential surface 32 of the plug 16 becomes spin-welded to the inner surface 28 of the housing 12. As will be readily understood by those of ordinary skill in the art, the spin-weld is created when the parts fuse together as a result of the heat generated by the friction between the rapidly spinning parts.

For example, the housing 12 can be held in a fixed position, and the mechanical drive device 38 is coupled to the plug 16 via the cooperation of the pins 40 with the axially-extending blind bores 36 (or the radially-extending ribs 215 illustrated in FIG. 4). The mechanical drive device 38 rotates the plug 16 relative to the housing 12 and moves the plug 16 into the open end 30 of the housing 12. The plug 16 is rotated about the longitudinal axis A and inserted into the open end 30 of the housing 12 simultaneously to create an annular interface, or annular frictional weld, between the outer circumferential surface 32 of the plug 16 and the inner surface 28 of the housing 12.

In some embodiments of the present invention, the plug 16 and/or the housing 12 can be rotated in one direction (i.e., clockwise or counter-clockwise). In other embodiments, the plug 16 and/or the housing 12 can be oscillated by rotating the plug 16 and/or the housing 12 a first amount in a first direction (e.g., clockwise) and then rotating the plug 16 and/or the housing 12 a second amount in a second direction opposite the first direction (e.g., counter-clockwise). The first amount does not need to be equal to the second amount, and in fact, the first amount can gradually increase and the second amount can gradually increase.

In some embodiments of the present invention, the plug 16 is inserted into the open end 30 of the housing 12 prior to rotation of the plug 16 and/or the housing 12. In other embodiments, the plug 16 is inserted at least partially into the open end 30 of the housing 12 prior to rotation of the plug 16 and/or the housing 12, and the plug 16 and/or the housing 12 are then axially moved relative to the other of the plug 16 and the housing 12 as the plug 16 and/or the housing 12 continue to be rotated.

The rotation of the plug 16 and/or the housing 12 continues until a predetermined interface temperature of the interface between the outer circumferential surface 32 and the inner surface 28 has been achieved, a predetermined number of rotations has been achieved, a predetermined number of oscillations has been achieved, a user or a control system aborts the process, and a combination thereof.

The movement of the plug 16 into the open end 30 of the housing 12 and/or the movement of the housing 12 over the plug 16 continues until at least one of the plug 16 and the housing 12 has been moved a predetermined distance, a predetermined insertion force from moving the plug 16 into the open end 30 of the housing 12 has been achieved, a predetermined insertion force from moving the open end 30 of the housing 12 over at least a portion of the plug 16 has been achieved, a first interface temperature between the outer circumferential surface 32 and the inner surface 28 has been achieved, at least a portion of the bottom surface 42 of the plug 16 has contacted the first frit 18 within the housing 12, at least a portion of the bottom surface 42 of the plug 16 has contacted the at least one chromatography medium 14 within the housing 12, a user or a control system aborts the operation, and a combination thereof.

FIG. 3 illustrates a cartridge 100 according to another embodiment of the present invention, wherein like numerals represent like elements to the embodiments described above. The cartridge 100 includes a housing 112 adapted to receive at least one chromatography medium 114, at least one frit 118 or other porous member (only one shown in FIG. 3 for simplicity), and a plug 116. The housing 112 includes an outer surface 126, an inner surface 128, an open end 130 and a longitudinal axis B.

The plug 116 includes an inner portion 117 dimensioned to be received within the open end 130 of the housing 112. The inner portion 117 of the plug 116 includes an outer circumferential surface 132, at least a portion of which is fused with at least a portion of the inner surface 128 of the housing 112 following the spin-welding method described above. The plug 116 includes an outer annular portion 119 integrally formed with the inner portion 117 of the plug 116. The outer annular portion 119 extends along the outer surface 126 of the housing 112 adjacent the open end 130. The outer annular portion 119 forms an aesthetic shroud or canopy to at least partially conceal from view the inner portion 117 of the plug 116. The aesthetic shroud formed by the outer annular portion 119 can also conceal at least a portion of the fused interface between the outer circumferential surface 132 of the plug 116 and the inner surface 128 of the housing 112 to form a more aesthetically-pleasing cartridge 100.

FIG. 5 illustrates a cartridge 300 according to another embodiment of the present invention, wherein like numerals represent like elements to the embodiments described above. The cartridge 300 includes a housing 312 adapted to receive at least one chromatography medium 314, a first frit 318, a second frit 320, a first plug 316, and a second plug 416. The housing 312 includes an outer surface 326, an inner surface 328, a first open end 330, a second open end 430, and a longitudinal axis C. The first plug 316 and the second plug 416, similar to the plug 116 shown in FIG. 3 and described above, each include an inner portion 317 and 417, respectively, and an outer annular portion 319 and 419, respectively. The inner portions 317 and 417 of the first plug 316 and the second plug 416 each include an outer circumferential surface 332 and 432, respectively, at least a portion of which can be fused with at least a portion of the inner surface 328 of the housing 312, as described above with respect to the plug 116. The cartridge 300 can have any length desired, enabled at least partially by forming the housing 312 to a desired length. The first plug 316 and the second plug 416 can be fused to the housing 312 of the desired length to tightly compress the at least one chromatography medium 314 within the housing 312 to form the cartridge 300 to the desired length.

In the embodiment illustrated in FIG. 5, an inlet 311 of the cartridge 300 is defined in a tube 335 of the first plug 316, and an outlet 313 of the cartridge 300 is defined in a tube 325 of the second plug 416. The tubes 325 and 335 are similar to the tubes 25 and 35 shown in FIGS. 1 and 2. However, it should be noted that in other embodiments, the first plug 316 can be identical to the second plug 416, such that the tubes defining the inlet 311 and the outlet 313 are also identical.

The first plug 316 and the second plug 416 also each include a flange 331 and 431, respectively. The flanges 331 and 431 can be used to couple at least one of the first plug 316 and the second plug 416, respectively, to a mechanical drive device during manufacturing of the cartridge 300; to couple at least one of the cartridge 300, the first plug 316 and the second plug 416 to a variety of packing and storage materials for transportation and storage; and/or to couple the cartridge 300 to other equipment in a chromatography system during use.

Various features and aspects of the invention are set forth in the following claims.

The invention claimed is:

1. A chromatography cartridge comprising:
a tubular housing having a first open end, a second open end, an outer surface, and an inner surface, the tubular housing defining an interior volume;
a first plug including an annular groove adapted to receive the first open end of the tubular housing, a first portion of the first plug positioned through the first open end and into the interior volume and having an outer circumferential surface, a substantial portion of the outer circumferential surface having a length greater than the thickness of the tubular housing and being fused to the inner surface of the tubular housing, and a second portion of the first plug positioned outside the interior volume and extending toward the second open end, the second portion of the first plug extending along and overlapping a portion of the outer surface of the tubular housing;
a first frit positioned in the interior volume, the first frit having a first surface oriented substantially parallel to a lateral surface of the first portion of the first plug, the first surface of the first frit being in contact with the lateral surface of the first portion of the first plug;
a first opening extending through the first plug, the first opening being in fluid communication with the interior volume, the first plug including a protruding extension through which the first opening extends;
a second plug including an annular groove adapted to receive the second open end of the tubular housing, a first portion of the second plug positioned through the second open end and into the interior volume, and having an outer circumferential surface, a substantial portion of the outer circumferential surface having a length greater than the thickness of the tubular housing and being fused to the inner surface of the tubular housing, and a second portion of the second plug positioned outside of the interior volume and extending toward the first open end, the second portion of the second plug extending along and overlapping a portion of the outer surface of the tubular housing;
a second opening extending through the second plug, the second opening being in fluid communication with the interior volume; and
a second frit positioned in the interior volume, the second frit having a first surface oriented substantially parallel to a lateral surface of the first portion of the second plug, the first surface of the second frit being in contact with the lateral surface of the first portion of the second plug.

2. The chromatography cartridge set forth in claim 1, wherein the substantial portion of the outer circumferential surface of the first and second plugs is frictionally-welded to the inner surface of the tubular housing.

3. The chromatography cartridge set forth in claim 1, wherein the substantial portion of the outer circumferential surface of the first and second plugs is spin-welded to the inner surface of the tubular housing.

4. The chromatography cartridge set forth in claim 1, wherein one of the first plug and the second plug comprises a first portion positioned within the open end of the tubular housing and a second portion positioned to extend outwardly of the respective open end of the tubular housing.

5. The chromatography cartridge set forth in claim 4, wherein the second portion of one of the first plug and second plug extends along at least a portion of an outer surface of the tubular housing to at least partially conceal the first portion of the respective plug.

6. The chromatography cartridge set forth in claim 1, wherein the cartridge is disposable.

7. The chromatography cartridge set forth in claim 1, wherein the cartridge has a longitudinal axis, and further comprising a plurality of axially-directed bores extending through an upper surface of one of the first plug and second plug to provide a coupling site for a mechanical drive device.

8. The chromatography cartridge set forth in claim 1, further comprising at least one radially-extending rib on an upper surface of the plug to provide coupling between a mechanical drive device and the plug.

9. The chromatography cartridge set forth in claim 1, further comprising a cover positioned over one of the first plug and second plug and tubular housing to hide at least a portion of the respective plug.

10. The chromatography cartridge set forth in claim 1, wherein the outer circumferential surface of one of the first plug and second plug is fused to the inner surface of the tubular housing adjacent the respective open end of the tubular housing.

11. The chromatography cartridge set forth in claim 1, wherein the second portion of the first plug includes an axial length greater than an axial length of the first portion of the first plug.

12. The chromatography cartridge set forth in claim 11, wherein the second portion of the second plug includes an axial length greater than an axial length of the first portion of the second plug.

13. The chromatography cartridge set forth in claim 1, wherein the second portion of the first plug includes an inner circumferential surface that is fused to the outer surface of the tubular housing.

14. The chromatography cartridge set forth in claim 13, wherein the second portion of the second plug includes an inner circumferential surface that is fused to the outer surface of the tubular housing.

15. A chromatography cartridge comprising
a tubular housing having an inlet, an outlet, a first open end and a second open end, a longitudinal axis and an inner surface;
a first porous disk positioned within the tubular housing adjacent the inlet;
a second porous disk positioned within the tubular housing adjacent the outlet;
at least one chromatography medium received in the tubular housing and disposed axially between the first porous disk and the second porous disk;
a first plug positioned within the first open end of the tubular housing, the first plug having a first lateral surface in contact with the first porous disk and a second surface outside of the tubular housing, the first plug including an annular groove adapted to receive the first open end of the tubular housing, a first portion of the first plug having an outer circumferential surface, at least a portion of the outer circumferential surface having a length greater than the thickness of the tubular housing and being fused to the inner surface of the tubular housing, the first plug including the inlet, and a second portion of the first plug positioned outside of the tubular housing and extending toward the second open end, the second portion of the first plug extending along and overlapping a portion of the outer surface of the tubular housing; and
a second plug positioned within the second open end of the tubular housing, the second plug having a first lateral surface in contact with the second porous disk and a second surface outside of the tubular housing, the second plug having an annular groove adapted to receive the second open end of the tubular housing, a first portion of the second plug having an outer circumferential surface, at least a portion of the outer circumferential surface having a length greater than the thickness of the tubular housing and being fused to the inner surface of the tubular housing, the second plug including the outlet.

16. The chromatography cartridge set forth in claim 15, wherein at least a portion of the outer circumferential surface of the first and second plugs is frictionally-welded to the inner surface of the tubular housing.

17. The chromatography cartridge set forth in claim 15, wherein at least a portion of the outer circumferential surface of the first and second plugs is spin-welded to the inner surface of the tubular housing.

18. The chromatography cartridge set forth in claim 15, wherein the outer circumferential surface of the first and second plugs is fused to the inner surface of the tubular housing adjacent the respective open end of the tubular housing.

19. The chromatography cartridge set forth in claim 15, wherein one of the first plug and second plug includes a first portion positioned within the open end of the tubular housing and a second portion positioned to extend outwardly of the respective open end.

20. The chromatography cartridge set forth in claim 19, wherein the second portion of one of the first plug and second plug extends at least partially along an outer surface of the tubular housing to at least partially conceal the first portion of the respective plug.

21. The chromatography cartridge set forth in claim 15, further comprising at least one axially-extending bore extending through an upper surface of one of the first plug and second plug to provide a coupling site for a mechanical drive device.

22. The chromatography cartridge set forth in claim 15, further comprising at least one radially-extending rib on an upper surface of the plug to provide coupling between a mechanical drive device and the plug.

23. The chromatography cartridge set forth in claim 15, wherein the second portion of the first plug includes an axial length greater than an axial length of the first portion of the first plug.

24. The chromatography cartridge set forth in claim 23, wherein the second portion of the second plug includes an axial length greater than an axial length of the first portion of the second plug.

25. The chromatography cartridge set forth in claim 15, wherein the second portion of the first plug includes an inner circumferential surface that is fused to the outer surface of the tubular housing.

26. The chromatography cartridge set forth in claim 25, wherein the second portion of the second plug includes an inner circumferential surface that is fused to the outer surface of the tubular housing.

* * * * *